United States Patent
Reipa et al.

[11] Patent Number: 6,126,795
[45] Date of Patent: Oct. 3, 2000

[54] ELECTROENZYMATIC REACTOR AND METHOD FOR ENZYMATIC CATALYSIS

[75] Inventors: Vytautas P. Reipa, North Potomac; Vincent L. Vilker, Chevy Chase, both of Md.

[73] Assignee: The United States of America as represented by the Secretary of Commerce, Washington, D.C.

[21] Appl. No.: 09/195,325

[22] Filed: Nov. 18, 1998

Related U.S. Application Data

[62] Division of application No. 08/976,992, Nov. 24, 1997, abandoned.
[60] Provisional application No. 60/031,508, Nov. 27, 1996.
[51] Int. Cl.[7] .............................. C25B 9/00; C25C 7/00; C25D 17/00
[52] U.S. Cl. .......................... 204/258; 204/252; 204/275
[58] Field of Search ........................... 205/413; 204/252, 204/258, 275

[56] References Cited

U.S. PATENT DOCUMENTS

| | | | |
|---|---|---|---|
| 3,919,052 | 11/1975 | Fresnel et al. | 435/286.1 |
| 4,318,784 | 3/1982 | Higgins et al. | 204/73 R |
| 4,655,885 | 4/1987 | Hill et al. | 204/72 |
| 4,761,208 | 8/1988 | Gram et al. | 204/275 |
| 5,403,450 | 4/1995 | Mellor et al. | 205/742 |
| 5,510,512 | 4/1996 | Strutz | 560/186 |

FOREIGN PATENT DOCUMENTS

WO8000453  3/1980  WIPO .

OTHER PUBLICATIONS

Albertson et al., "Spectroelectrochemical Determination of Heterogeneous Electron Transfer Rate Constants," Analytical Chemistry, vol. 51, No. 4, Apr. 1979, pp. 556–560.

Allen et al., "Surface Modifiers for the Promotion of Direct Electrochemistry of Cytochrome c," J. Electroanal. Chem., 178 (1984), pp. 69–86 no month available.

Armstrong, "Probing Metalloproteins by Voltammetry," Structure and Bonding, vol. 72, 1990, pp. 137–221 no month available.

Brewer et al., "Single Turnover Kinetics of the Reaction between Oxycytochrome $P-450_{cam}$ and Reduced Putidaredoxin," The Journal of Biological Chemistry, vol. 263, No. 2, Jan. 1988, pp. 791–798.

Brewer et al., "Single Turnover Studies with Oxy–cytochrome $P-450_{cam}$," Archives of Biochemistry and Biophysics, vol. 249, No. 2, Sep. 1986, pp. 515–521.

Eble et al., "NADH– and Oxygen–Dependent Multiple Turnovers of Cytochrome P–450–CAM without Putidaredoxin and Putidaredoxin Reductase," Biochemistry 1984, vol. 23, No. 9, pp. 2068–2073 no month available.

Elliott et al., "Electrochemical Properties of Polycrystalline Tin Oxide," J. Electrochem. Soc.: Electrochemical Science, Nov. 1970, pp 1343–1348.

Estabrook et al., "Application of Electrochemistry for P450–Catalyzed Reactions," Methods in Enzymology, vol. 272, 1996, pp. 44–51 no month available.

Faulkner et al., "Electrocatalytically Driven ω–hydroxylation of fatty acids using cytochrome P450 4A1," Proc. Natl. Acad. Sci. USA, vol. 92, Aug. 1995, pp. 7705–7709.

(List continued on next page.)

*Primary Examiner*—Kathryn Gorgos
*Assistant Examiner*—Eama Wong
*Attorney, Agent, or Firm*—Christie Parker & Hale

[57] ABSTRACT

An electroenzymatic reactor comprises a reaction vessel having a working electrode compartment. Within the working electrode compartment is a reactor solution containing a redox enzyme, a redox carrier, and an oxidizable or reducible substrate. Also within the working electrode compartment is a reference electrode and a metal oxide working electrode capable of being held close to the redox potential of the redox carrier. A counter electrode is provided outside the working electrode compartment. Necessary molecular oxygen or hydrogen is supplied to the reaction by water electrolysis at the counter electrode. Hydrogen peroxide that is generated at the working electrode or counter electrode is decomposed by a screen situated near the hydrogen-peroxide generating electrode.

39 Claims, 1 Drawing Sheet

OTHER PUBLICATIONS

Fruetel et al., "Calculated and Experimental Absolute Stereochemistry of the Styrene and β–Methylstyrene Epoxides Formed by Cytochrome P450$_{cam}$," Journal American Chemical Society, vol. 114, No. 18, 1992, pp. 6987–6993 no month available.

Grayson et al., "Tetralin as a Substrate for Camphor (Cytochrome P450) 5–Monooxygenase," Archives of Biochemistry and Biophysics, vol. 332, No. 2, Aug. 1996, pp. 239–247, Article No. 0338.

Gunsalus et al., "Cytochrome P–450$_{cam}$ Substrate and Effector Interactions," Annals New York Academy of Sciences, 107 (1973), pp. 107–117 no month available.

Ishimura, Yuzura, "Oxygen Activation and Transfer," Cytochrome P–450, Second Edition, pp. 80–91, 186–205 (1993). no month available.

Kazlauskaite et al., "Direct electrochemistry of cytochrome P450cam," Chem. Commun., 1996, pp. 2189–2190 no month available.

Lipscomb et al., "Autooxidation and Hydroxylation Reactions of Oxygenated Cytochrome P–450cam," The Journal of Biological Chemistry, vol. 251, No. 4, Feb. 1976, pp. 1116–1124.

Mohr, et al., "Aspects of Application of Cytochrome P–450 and Related Systems in Substrate Hydroxylation," Abstr., Pharmazie, Jul. 1978, vol. 33, No. 7, pp. 415–418.

Mohr, et al.; "Hemoproteins and Related Models in Hydroxylation Reactions of Organic Compounds," Abstr., J. Mol. Catal., 1981, vol. 13, No. 2, pp. 147–163 no month available.

Mohr, et al., "Use of Cytochrome P–450 and Iron Porphyrin as Catalysts in Hydroxylation Reactions in Combination With Electrochemical Systems," Abstr., Appl. Biochem. Microbiol., vol. 18, No. 4, 1982, pp. 377–384 no month available.

Mueller, Ernest J. , Paul J. Loida, and Stephen G. Sligar, "Twenty–five Years of P450cam Research," Cytochrome P450, Structure, Mechanism, and Biochemistry, Second Edition, 1995, Chapter 3, pp. 83–124. no month available.

Nishiyama et al., "Aminosilane modified indium oxide electrodes for direct electron transfer of ferredoxin," Journal of Electroanalytical Chemistry, vol. 373, (1994), pp. 255–258 no month available.

Pederson et al., "Redox and Ligand Dynamics in P450cam–Putidaredoxin Complexes," Microsomes and Drug Oxidations, Proceedings of the Third International Symposium Berlin, Jul. 1976, pp. 274–283.

Pugh, "Immobilized Redox Enzymes and Their Use as Catalysts for Fine Chemical Synthesis," Abstr., NATO ASI Ser., Ser. C, 1986, 178 (Enzymes Catal. Org. Synth.), pp. 217–232 no month available.

Pochapsky et al., "An NMR–Derived Model for the Solution Structure of Oxidized Putidaredoxin, a 2–Fe, 2–S Ferredoxin from Pseudomonas," Biochemistry, vol. 33, No. 21, 1994, pp. 6424–6432 no month available.

Reipa et al., "Surface–enhanced Raman spectroscopy (SERS) evidence of charge transfer between putidaredoxin and a silver electrode," Journal of Electroanalytical Chemistry, 395, Jan. 1995, pp. 299–303.

Reipa et al., "A direct electrode–driven P450 cycle for biocatalysis," Proc. Natl. Acad. Sci. USA, vol. 94, Dec. 1997, pp. 13554–13558.

Reipa et al., "Spectroscopic Real–Time Ellipsometry of Putidaredoxin Adsorption on Gold Electrodes," Abstr., Langmuir, 1997, vol. 13, No. 13, pp. 3508–3514 no month available.

Ryan et al., "Some Considerations in Spectroelectrochemical Evaluation of Homogeneous Electron Transfer Involving Biological Molecules," Analytical Chemistry, vol. 47, No. 6, May 1975, pp. 885–890.

Scheller, et al., "Electrochemical Investigations on the Oxygen Activation by Cytochrome P–450," Abstr., Acta. Biol. Med. Ger., vol. 38, No. 2–3, 1979, pp. 503–510 no month available.

Schubert, et al., "Application of Cytochrome P–450 in Enzyme Reactors and Enzyme Electrodes," Abstr., Pharmazie, 1985, vol. 40, No. 4, pp. 235–239 no month available.

Sligar et al., "Chemical mechanisms for cytochrome P–450 hydroxylation: Evidence for acvlation of heme–bound dioxygen," Proc. Natl Acad. Sci USA, vol. 77, No. 3, Mar. 1980, pp. 1240–1244.

Sligar et al., "A thermodynamic model of regulation: Modulation of redox equilibria in camphor monoxygenase," Proc. Nat. Acad. Sci USA, vol. 73, No. 4, Apr. 1976, pp. 1078–1082.

White et al., "Regioselectivity in the Cytochromes P–450: Control by Protein Constraints and by Chemical Reactivities," Archives of Biochemistry and Biophysics, vol. 228, No. 2, Feb., 1984, pp. 493–502.

Wong et al., "Characterization of Mercaptoethylamine–Modified Gold Electrode Surface and Analyses of Direct Electron Transfer to Putidaredoxin," American Chemical Society, Dec. 1995, pp. 4818–4822.

Wong, et al., "Development of a Novel Bioconversion Process Based on a P450cam Subsystem Driven by an Electrode Instead of NADH," Abstr. Pap. Am. Chem. Soc., 1996, 211 Meet., Pt. 1 no month available.

Yildirim, "Autooxidation and Hydroxylation Reactions of Oxygenated Cytochrome P–450cam," University of California, 1991, pp. 1–16 no month available.

Zhang et al., "Direct electron injection from electrodes to cytochrome P450 $_{cam}$III biomembrane–like films," J. Chem. Soc., Faraday Trans., 1977, pp. 1769–1774 no month available.

ELECTROENZYMATIC REACTOR AND METHOD FOR ENZYMATIC CATALYSIS

CROSS-REFERENCE TO RELATED APPLICATION

This application is a divisional of U.S. application Ser. No. 08/976,992, filed Nov. 24, 1997, now abandoned which claims priority of Provisional U.S. patent application Ser. No. 60/031,508, filed Nov. 27, 1996, the subject matter of which is fully incorporated herein.

ACKNOWLEDGMENT OF GOVERNMENT SUPPORT

This invention was made with government support under Department of Commerce Grant No. 70NANB4H1614 and NSF Grant No. CATS9313009. The government has certain rights in the invention.

FIELD OF THE INVENTION

The present invention relates to a reactor and method for the selective transformation of substrates using redox enzymes, and, more particularly, to a reactor and method in which reducing equivalents are supplied to or removed from the redox enzymes electrochemically.

BACKGROUND OF THE INVENTION

Biocatalytic oxidation and reduction can be used to transform substrates with high regio- and/or stereo-selectivity. For example, biocatalytic oxidation can be used to stereospecifically hydroxylate hydrocarbons that possess no prior functional groups. Products of biocatalytic oxidation and reduction have widespread commercial application. For example, oxygenated hydrocarbons are becoming increasingly important in a range of applications, including use as blending stock for motor gasoline, intermediates for the manufacture of new less-polluting chemicals (e.g., biodegradable polymers), starting materials for synthesis of new, high-value-added products (e.g., enantiomeric pharmaceuticals), and wastewater detoxification technologies.

The cytochrome P450 enzymes are widely distributed throughout nature and participate in diversified metabolic reactions as the oxygen-activating component of monooxygenase systems, or as the dehalogenation agent of reductase systems. Their unique oxygenation chemistry and substrate specificity offer the opportunity to develop enzymatic systems for synthesizing fine chemicals, sensing biochemically active compounds, and detoxifying environmental contamination. A major hurdle to implementation of P450 catalysis for commercial syntheses is the requirement for stoichiometric amounts of freely dissociated cofactors, such as NADH (nicotinamide adenine dinucleotide hydride) and/or redox partner proteins, which supply necessary reducing equivalents. This requirement is currently met either as an additional nutrient cost during in vivo whole cell biocatalysis (fermentation) or as a cost of supplying fresh cofactor along with target substrate during in vitro biocatalysis.

A particular member of the cytochrome P450 enzymes, cytochrome CYP101 (E.C. 1.14.15.1) monooxygenase, is found in the bacterium *Pseudomonas putida* PpG786 when it is cultured on camphor. CYP 101 catalyzes camphor hydroxylation at the 5-exo position. Investigation has also been done on stereospecific hydroxylation of other substrates (Fruetel et al., *J. Am. Chem. Soc.*, 114, 6987–6993 (1992); Grayson et al., *Arch. Biochem Biophys.*, 332, 239–247 (1996)) as well as dehalogenation reactions (Koe & Vilker, *biotechnology Progress*, 9, 608–614 (1993)).

In its normal physiological role (i.e., natural cycle), this three-protein enzyme system hydroxylates camphor using NADH as the source of reducing equivalents. The reactions require NADH as well as two protein cofactors. The overall biocatalytic cycle involves many individual reactions. The two electrons necessary for the conversion of the substrate are supplied by reduced putidaredoxin (Pdx), a 2Fe-2S protein, which mediates the transfer of the electrons from NADH, and the FAD-containing putidaredoxin reductase (PdR) to the heme active center of the cytochrome CYP101. In addition to being an electron mediator, Pdx is also an "effector" for product release in the final step of the cycle. The overall reaction is thermodynamically controlled, and redox potential and substrate binding are modulated by the cytochrome spin-state equilibrium.

In industrial applications, NADH is lost by decomposition and must be replenished to continue the reaction. NADH is expensive, however, and thus economic feasibility requires that simple, effective and stable methods for cofactor recycling be found. Electrochemical cofactor regeneration can meet these requirements.

Some attempts have been made to use electrodes to supply the reducing power for driving P450 catalytic cycles. Bioelectrochemical processes have been described in which electrons are transferred directly (without mediators) between an electrode and redox-active biological material, such as an enzyme or protein, using various modified metal or graphite electrodes. Such processes suffer, however, from either inefficiency (low redox reaction rates) or rapid decline in activity due to component fouling by proteins.

Higgens et al. (U.S. Pat. No. 4,318,784) and Armstrong (*Structure and Bonding*, 72, 137–221, 1990) describe using metal and graphite electrodes modified with organic absorbates for the electron transfer to and from various redox-active biomolecules. These systems are inefficient and/or unstable, however, when applied to hydroxylation of organic compounds by the P450 cycle. Some of the problems with these systems include (i) modifier instability in the required potential range, (ii) irreversible adsorption of protein constituents leading to electrode fouling, and (iii) protein denaturation. See also Kazlauskaite et al. (*Chem. Commun.*, 2189–2190, 1996) and Zhang et al. (*J. Chem. Soc. Faraday Trans.*, 93, 1769–1774, 1997), which describe direct electron transfer from carbon-based electrodes to CYP101. The direct electron transfer study of Kazlauskaite et al. showed reversible electrochemical response from glassy carbon electrodes, corresponding to the first of the two electron transfers to CYP101 required to initiate the catalytic cycle, while Zhang et al. showed direct electron transfer from lipid-modified pyrolytic graphite electrodes to CYP101. Neither Kazlauskaite nor Zhang demonstrated oxygenase enzyme activity.

Faulkner et al. (*Proc. Natl. Acad. Sci. USA*, 92, 7705–7709, 1995) have shown mediated, electrode-driven biocatalysis using cobalt (III) sepulchrate to transfer electrons to rat recombinant liver P450 fusion proteins. In these mediated biocatalysis studies, the electrolysis enzyme turnover rate was comparable with the NADPH-driven cycle for a number of recombinant fusion microsomal P450 enzymes. See also Estabrook et al. (*Methods in Enzymology, Cytochrome P450, Part B*, eds. Johnson & Waterman, 44–50, 1996). The drawback to this method is the use of the cobalt mediator, which is expensive and difficult to remove from the reactants and products.

Previous investigation was done on the use of polycrystalline gold and silver electrodes modified by immobilizing ionizable organic molecules in order to overcome the repulsive electrostatic interaction that arises when trying to reduce the negatively-charged Pdx at the electrode. Reversible oxidation/reduction cycling of Pdx on these electrodes was observed, but the response was short-lived. Both in situ, surface-enhanced Raman spectroscopic and ellipsometric measurements demonstrated rapid deterioration of the organic electrode modifier while the electrode was held at potentials less than −0.7 V.

A clear need exists for an electrode that can rapidly and continuously reduce Pdx while having a minimal effect on other reaction components. The successful electrode must not be irreversibly coated by other components, including CYP101. Additionally, in order for the cytochrome P450 to participate repeatedly as a catalyst in hydroxylation reactions, it must be provided continually with oxygen. However, oxygen plays a dual role in these reactions, acting as a co-reactant for product formation and oxidizing the reduced components, thus decreasing the turnover of reactant into product. Previously, oxygen was supplied to such reactions by contacting the reactor solution with atmospheric air, or by purging the reaction solution with pure oxygen gas. These methods are disadvantageous, however, because they increase the oxygen concentration so high as to stop the reaction at the initial stages (by taking up electrons from the working electrode or reduced reactants). As a result, the product yield is low. Thus, a need exists for a new method for supplying oxygen to the reaction that results in a higher product yield.

SUMMARY OF THE INVENTION

In one embodiment, the invention comprises an electroenzymatic reactor made up of a reaction vessel, optionally having a cover. The reaction vessel contains a working electrode compartment and preferably a counter electrode compartment. Within the working electrode compartment is a metal oxide working electrode capable of being held close to the redox potential of the redox carrier. Also within the working electrode compartment is a reference electrode and a reactor solution comprising a redox enzyme, a redox carrier, and an oxidizable or reducible compound. The reaction vessel also contains a counter electrode outside the working electrode compartment, and preferably within the counter electrode compartment. Preferably the working electrode compartment and counter electrode compartment are separated by a gas permeable separator.

In another embodiment, the invention comprises an electroenzymatic reactor comprising a working electrode compartment. Within the working electrode compartment is a reactor solution and a working electrode. The reactor solution contains a redox enzyme, a redox carrier, and an oxidizable or reducible compound. The working electrode is made of a least one material selected from antimony-doped tin oxide, fluorine-doped tin oxide, indium-tin oxide, titanium oxide, zinc oxide, iridium oxide, and ruthenium oxide. The reactor also comprises a counter electrode made of at least one material selected from platinum group metals, metal oxides, and carbon-based materials.

In another embodiment, the invention is directed to an electroenzymatic reactor for oxidizing or reducing a substrate comprising a reaction vessel having a working electrode compartment and optionally a counter electrode compartment. The working electrode compartment contains a working electrode and a reactor solution comprising a redox enzyme, a redox carrier, and an oxidizable or reducible substrate. Also within the reaction vessel, and preferably within a counter electrode compartment, is a counter electrode that is capable of supplying molecular oxygen or hydrogen to the working electrode compartment by water electrolysis. To increase the turnover rate, a cover is used to prevent the flow of atmospheric oxygen into the working electrode compartment and permit the escape of purged gas. Preferably all of the molecular oxygen or hydrogen that is necessary for oxidizing or reducing the substrate is supplied by the counter electrode. The reaction vessel contains at least one inert gas inlet to provide an inert gas purge to the reactor solution and to the head space above the reaction solution.

In another embodiment, the invention comprises an electroenzymatic reactor comprising a reaction vessel having a working electrode compartment containing a working electrode and a reactor solution containing a redox enzyme, a redox carrier, and an oxidizable or reducible substrate. A counter electrode is located outside the working electrode compartment. A screen is provided that is capable of catalyzing the decomposition of hydrogen peroxide that originates during oxygen reduction at the electrode having the more negative potential, e.g., the working electrode for oxygenation reactions and the counter electrode for dehydrogenation reactions. The screen is situated near, but not contacting, the electrode having the more negative potential.

In another embodiment, the invention is directed to a method for biocatalytically oxidizing or reducing a substrate, comprising exposing the substrate to a reactor solution in the presence of a working electrode. The reactor solution contains a redox enzyme and a redox carrier. The working electrode is made of a metal oxide that is capable of being held close to the redox potential of the redox carrier. The method preferably generates a turnover rate of at least about 0.1 nmoles product/min/nmole redox enzyme for at least about two hours.

In another embodiment, the invention is directed to a method for biocatalytically oxidizing or reducing a substrate, comprising exposing the substrate to the above-described reactor solution in the presence of a working electrode that is capable of directly supplying reducing equivalents to or directly removing reducing equivalents from the redox carrier. Molecular oxygen or hydrogen is supplied to the reactor solution by water electrolysis on a counter electrode, which is separated from the working electrode by a gas permeable separator. The flow of atmospheric oxygen into the working electrode compartment is prevented. Preferably all of the molecular oxygen or hydrogen that is necessary for oxidizing or reducing the substrate is supplied by the counter electrode.

In another embodiment, the invention is directed to a method for biocatalytically oxidizing or reducing a substrate, comprising exposing the substrate to the above-described reactor solution in the presence of a working electrode capable of directly supplying reducing equivalents to or directly removing reducing equivalents from the redox carrier. The method further involves decomposing hydrogen peroxide that is generated during oxygen reduction at the electrode having a negative potential using a screen situated near, but not contacting, that electrode.

In a particularly preferred embodiment of the invention, the reaction solution contains CYP101, or its mutants, as the redox enzyme and Pdx, or its mutants, as the redox carrier. The working electrode is made of antimony-doped tin oxide and the counter electrode is made of platinum. The working electrode is set at a potential of about −0.7 V (vs. Ag/AgCl reference electrode). Molecular oxygen is supplied to the reaction by water electrolysis at the counter electrode. Additionally, hydrogen peroxide generated during oxygen reduction at the working electrode is decomposed by a screen situated near, but not contacting, the working electrode. This embodiment eliminates the need for NADH and PdR and simplifies the catalytic cycle as much as possible while still retaining the high product specificity found in the natural cycle.

The reactors and methods of the present invention are particularly useful for the above-described CYP101 enzyme system, but can also be applied to related systems, for example, the methane monoxygenase, cytochrome P450's from other bacterial or mammalian mitochondrial sources, dioxygenases of similar molecular architecture, and reductases. In each, a dual-function redox carrier like Pdx is required in the catalytic cycle for carrying out electron transfer and for affecting product specificity and high turnover rates.

DESCRIPTION OF THE DRAWING

These and other features and advantages of the present invention will be better understood by reference to the following detailed description when considered in conjunction with the accompanying drawing, which is a cross-sectional schematic view of a reactor according to the present invention.

DETAILED DESCRIPTION

Figure 1:
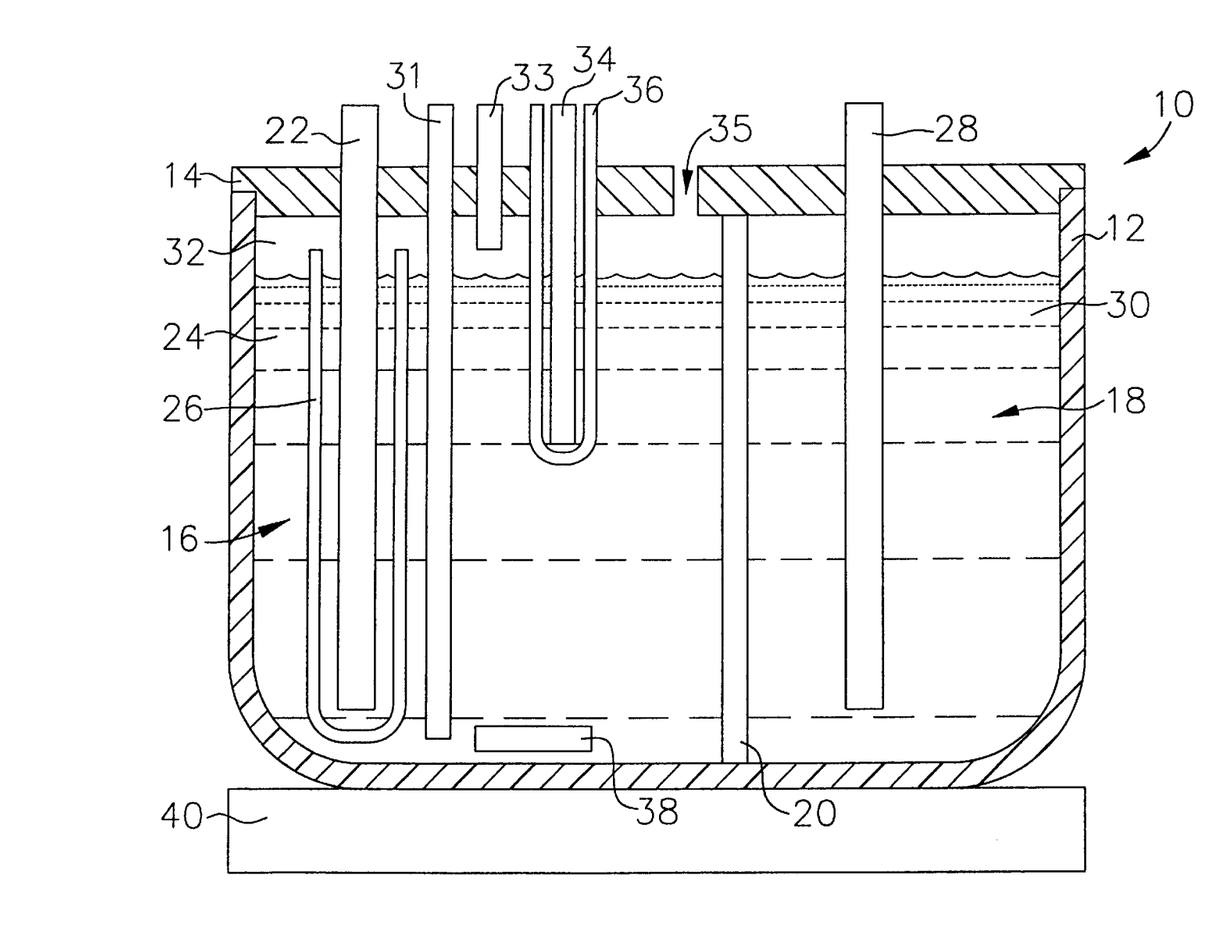

In one embodiment of the invention, as illustrated in the drawing, an electroenzymatic reactor comprises a reaction vessel containing at least one working electrode, at least one counter electrode, a reference electrode and a reactor solution. A substrate is introduced into the reactor and stereoselectively oxidized or reduced.

The reaction vessel 10 comprises a cell body 12 manufactured from a nonconductive, chemically inert and biocompatible material. Non-limiting examples of suitable materials for the cell body include glass, ceramic, polyethylene, polypropylene, polystyrene, polyvinylchloride, polycarbonate, polyester, polyvinyl fluoride, polymethyl methacrylate, and Teflon®.

The size of the reaction vessel 10 is not critical. An industrial-scale vessel, for example, can take the form of multiple small reactors linked in series. For example, a typical reactor battery could consist of fifty reactors, each having a volume of approximately 30 liters.

Preferably, the reaction vessel 10 further comprises a cover 14. The cover 14 prevents the flow of atmospheric oxygen into the reaction vessel 10. The cover 14 is equipped with a weep hole 35 (and optionally a valve) to release the pressure built up by gases purged into the reaction vessel 14. The cover 14 can be made of any suitable material, preferably a nonconductive, chemically inert and biocompatible material, nonlimiting examples of which are provided above.

The reaction vessel 10 has at least two compartments, the working electrode compartment 16 and the counter electrode compartment 18. The counter electrode compartment 18 is separated from the working electrode compartment 16 by means of a gas permeable separator 20, which allows passage of a buffer solution and gases between the compartments, but does not permit passage of the reactants, e.g., the redox enzyme and redox carrier. Suitable gas permeable separators 20 can be made, for example, from glass, dialysis membranes, and Teflon-based materials, such as Nafion™.

Within the working electrode compartment 16 is the working electrode 22 and the reactor solution 24. The working electrode 22 is made of a material that is inert to the other solution components in the working potential range. The material is also one that is not easily fouled by the solution components. Additionally, the material has redox activity towards the redox carrier, e.g., Pdx, and is capable of being held at or near the redox potential of the redox carrier, i.e., within ±0.5 volts of the redox potential. Preferably, the working electrode 22 is made of a metal oxide. Particularly preferred materials for the working electrode 22 include, but are not limited to, antimony-doped tin oxide, fluorine-doped tin oxide, indium-tin oxide, titanium oxide, zinc oxide, iridium oxide, and ruthenium oxide. More preferably, the working electrode 22 comprises antimony-doped tin-oxide, with up to 9% antimony, deposited on glass or any other suitable material. Other working electrodes 22 particularly well-suited for use in the present invention include reactively sputtered tin-oxide, tin-oxide lumps soaked in PtCl solution and heated to 500° C., reactively sputtered iridium-oxide on alumina or other suitable material, and metallic tin anodized according to the method described in E. Giani and R. Kelley, *J. Electrochemical Soc.*, 121, 394 (1974), the disclosure of which is incorporated herein by reference.

Preferably, the ratio of the surface area of the working electrode 22 to the volume of the reactor solution 24 is selected to maximize the volumetric production rate of the product. Because the limiting step of the process is the electron transfer between the working electrode 22 and the redox carrier, it is desirable to have this ratio as large as possible, for example, about 100 m$^{-1}$.

The potential of the working electrode 22 is selected with the understanding that the initial product formation rate increases with overvoltage, but at the expense of the bioreactor system sustainability. For example, for the CYP101 system, the potential of the working electrode 22 is preferably about −0.5 V to about −0.9 V, more preferably about −0.7 V, versus a Ag/AgCl reference electrode. For other redox carrier/redox enzyme systems, this potential range may be expanded to about +1 V to −1 V. Also the potential may be continuously varied within this range. All potentials referred to in the specification and claims are referenced to a Ag/AgCl reference electrode.

The reactor solution 24 comprises a buffer solution, a redox enzyme, a corresponding redox carrier, and a substrate. The buffer solution preferably contains a source of chloride ions, such as KCl, NaCl, MgCl$_2$, LiCl, and CsCl, which contribute to protein stabilization and the efficiency of the metal oxide working electrodes 22 for directly reducing proteins. More preferably, the buffer solution contains KCl and MgCl$_2$. In an alternate embodiment, the buffer solution contains other halide ions.

The buffer solution is maintained at a pH where the reactor solution components are stable. For example, in the CYP101 system, the pH is maintained from about 7.2 to 7.6, more preferably about 7.4. The pH can be maintained by using any biocompatable buffer, such as Tris-HCl or Hepes buffers. Although the temperature of the buffer solution preferably is less than the temperature of protein denaturation, there is no particularly preferred minimum temperature. Even frozen aqueous buffer solutions can be used in combination with liquid organic solvents that are not water soluble. However, decreasing the temperature of the buffer solution tends to decrease the reaction rate.

As used herein, the term "redox enzyme" refers to an enzyme in the oxidoreductase class as defined in M. Dixon & E.C. Webb, *Enzymes*, 3d Ed., pp. 218–220, Academic Press: New York, 1979, the disclosure of which is incorporated herein by reference. As used herein, the term "redox carrier" refers to a cofactor, as described in Dixon and Webb, that is reduced by one substance and oxidized by another. A preferred redox enzyme and corresponding redox carrier is CYP101 and Pdx. The concentrations of the redox enzyme and redox carrier affect both the total yield of the final product and the turnover rate. Preferably, the redox carrier concentration is at least 10 times greater than the redox enzyme concentration. For the CYP101 system, for example, the Pdx can be present in a concentration of from about 5 $\mu$M to 10 mM, although availability and cost of the protein limit the concentrations that can be commercially employed.

Preferably the redox enzyme and redox carrier are purified using standard methods, for example, ion-exchange chromatography and/or size exclusion chromatography. The redox enzyme and redox carrier are preferably at least about 50% pure, more preferably at least about 95% pure, still more preferably at least about 97% pure, based on measurement by high-resolution two-dimensional gel electrophoresis.

The substrate is an oxidizable or reducible compound. As used herein, an oxidizable compound is one that is capable of being biocatalytically oxidized. Typical biocatalytic oxidation reactions include, for example, oxygenation as well as conversion of an alcohol to a ketone or aldehyde. A reducible compound is one that is capable of being biocatalytically reduced. Typical biocatalytic reduction reactions include, for example, addition of hydrogen, conversion of a nitrate to a nitrite and/or nitrogen, and conversion of a ketone or aldehyde to an alcohol.

Examples of suitable substrates include, but are not limited to, alkanes, alkenes, aromatic hydrocarbons, nitrogen-based compounds, sulfur-based compounds, and phosphorus-based compounds. Substrates that are particularly suitable for the CYP101 system include camphor, tetralin, dibromochloropropane, styrene, naphthalene, decalin, and C2- to C4- halocarbons of varying halogen substitution. The substrate can be introduced into the reactor solution 24 as an aqueous solution or with organic cosolvents or surfactants to enhance the substrate solubility and turnover rates.

Within the counter electrode compartment 18 is a counter electrode 28 and a buffer solution 30. Preferably, the buffer solution 30 in the counter electrode compartment 18 is the same as the buffer solution contained in the reactor solution 24 in the working electrode compartment 16.

The counter electrode 28 can be made of any suitable material that is noncorrosive in the reactor solution 24. A preferred counter electrode 28 is made of a material that is capable of supplying oxygen or hydrogen to the reaction vessel during the reaction, such as a platinum group metal, a metal oxide, and/or a carbon-based material. Particularly preferred counter electrode materials include palladium; ruthenium; platinum as wires, sheets or thin films; ruthenium oxide; glassy carbon; reticulated carbon; titanium dioxide; and mixed metal oxides.

The ratio of the surface area of the working electrode 22 to the surface area of the counter electrode 28 is selected to keep the counter electrode potential between the oxygen and halogen gas evolution potentials, and is dependent on the composition of the working and counter electrodes. For example, when the working electrode 22 comprises antimony-doped tin-oxide and the counter electrode 28 comprises platinum, the preferred ratio ranges from about 8:1 to 10:1.

Molecular oxygen or hydrogen necessary for the reaction preferably is supplied by water electrolysis at the counter electrode 28 through the gas permeable separator 20. Alternatively, the molecular oxygen or hydrogen is supplied by purging the solution with a gas mixture containing oxygen or hydrogen. However, this method is less preferred, particularly with respect to oxygen, because purged oxygen increases the rapid reoxidation of the redox carrier before it can deliver its reducing power to the redox enzyme.

Additionally, an inert gas inlet is provided through which argon or another suitable inert gas (e.g., nitrogen or helium) is purged into the reactor solution 24 to displace the dissolved gases, primarily oxygen or hydrogen. In one embodiment, the inert gas inlet comprises two tubes 31 and 33 inserted through holes in the cover 14 of the reaction vessel 10. Tube 31 has two ends, one situated in the reactor solution 24 near the bottom of the reaction vessel 10 and the other connected to a source of inert gas. Tube 33 has also two ends, one situated in the head space 32 (i.e., the volume between the reactor solution and the cover) and the other connected to a source of inert gas. The tubes 31 and 33 can be made of any suitable material, preferably nonconductive, chemically inert and biocompatible material, nonlimiting examples of which include glass, ceramic, polyethylene, polypropylene, polystyrene, polyvinylchloride, polycarbonate, polyester, polyvinyl fluoride, polymethyl methacrylate, and Teflon®. Other means of introducing inert gas into the reactor solution 24 and head space 32 include adding a turbine impeller to the reactor solution or adding a sparge plate, tube or frit at the bottom of the reactor vessel 10. Preferably, before the reaction, both the head space 32 and the reactor solution 24 are purged with argon for about 30 minutes. This allows the reaction to begin with oxygen-free buffer to obtain maximum turnover rates. The argon purge is then supplied during the reaction to the head space 32.

A reference electrode 34 is also included in the reactor. Any suitable reference electrode 34 can be used, such as a calomel reference electrode or a normal hydrogen electrode. A preferred reference electrode 34 used in the present invention is a standard Ag/AgCl electrode, available from Abtech Inc. (Yardly, Pa.). The reference electrode 34 is positioned in the working electrode compartment 16, but separated from the reactor solution 24 by an ion-permeable membrane 36. Preferably, the reference electrode 34 is in a KCl solution.

A screen 26 is also provided in the reaction vessel 10 to catalyze the decomposition of trace hydrogen peroxide generated during oxygen reduction at the electrode having a more negative potential. Hydrogen peroxide is an extremely reactive compound and destroys the enzymes after a very short time. In general, for oxygenation reactions, the working electrode 22 has a more negative potential with respect to the counter electrode, and the screen 26 is situated as close as possible to the working electrode 22 without contacting it. For dehydrogenation reactions, the counter electrode 28 has a more negative potential with respect to the working electrode, and the screen 26 is situated near, but not contacting, the counter electrode 28.

The screen 26 can be made of any suitable non-corrosive metal, such as platinum, iridium, nickel, rhodium and cobalt.

A preferred screen 26 is a platinum mesh that surrounds the hydrogen peroxide-generating electrode. In an alternate embodiment, the screen 26 is a platinum sheet placed in close proximity to the hydrogen peroxide-generating electrode. Preferably, the screen 26 has a surface area greater than or equal to the surface area of the hydrogen peroxide-generating electrode.

A stirring mechanism is provided to produce efficient mass transport to and from the working electrode. A preferred stirring mechanism is a magnetic stir bar 38 in combination with a magnetic plate 40. Other solution stirring mechanisms include, for example, motor-driven stirrers, pumping, ultrasound, and electrode rotation or vibration.

As used herein, the term "turnover rate" refers to the ratio of product concentration to enzyme concentration per unit time. The optimum turnover rate depends on the product being made. For example, for stereospecific oxygenation of camphor, an average turnover rate preferably of at least about 0.1 $min^{-1}$, more preferably at least about 10 $min^{-1}$, still more preferably of at least about 30 $min^{-1}$, is attained for at least about 2 hours.

As used herein, the term "product yield" refers to the percentage of substrate that is stereospecifically oxidized or reduced during the reaction. Preferably, the reactors and methods of the present invention are capable of achieving a product yield of at least about 50 percent, more preferably at least about 90 percent.

EXAMPLES

The following non-limiting examples are illustrative of the invention, its construction, and its operation.

Protein Preparation

In the following examples, the proteins that make up the CYP101 system were derived from *Escherichia coli* clones (DH5-α), each containing a single plasmid for one of the three CYP101 subunit proteins (CYP101, Pdx, Pdr). The proteins were then purified using ion-exchange chromatography and size exclusion chromatography. The final protein preparations were at least 95% pure. On the basis of absorbance ratios, the mole fraction purity ×100 of each subunit protein was greater than 90. In addition, several preparations of the proteins were examined by high-resolution two-dimensional gel electrophoresis and by imaging analysis, and the mole fraction purity ×100 was estimated to be greater than 97 for each protein.

Electrode Preparation

The working electrodes used in the following examples were antimony-doped, tin-oxide coated (0.3 μm thickness) glass slides (4×2 cm, Delta Technologies, Stillwater, Min.), with donor concentration as determined from Mott-Schottky plots ($N_d$=5×$10^{20}$ $cm^{-3}$). Prior to the biocatalysis experiments, the electrodes were soaked and sonicated in 1 M NaOH for approximately two hours, then rinsed with distilled water. They were activated in 15% HCl solution using a potential sweep between –0.5 and 1.5 V at 10 mV/s, and stored in distilled water. Film electrode resistance, as measured by a four point probe (Cascade Mictrotech, Inc., Model C4A-44 Beaverton, Oreg.), was 40–50 Ω/sq.

The reference electrode was a standard Ag/AgCl (3M KCl) reference micro-electrode (Abtech Inc. RE803). The counter electrode was made as a coil of 0.5 mm thick Pt wire.

Buffer Solution

The buffer media was prepared using 0.16 M aqueous KCl and 0.01 M aqueous $MgCl_2$, adjusted to about pH 7.4 with Tris-HCl buffer.

Electron Transfer Rate Measurements

Absorbance during the electrolysis was monitored using a thin layer (0.2 mm) cell comprised of two antimony-doped, tin oxide electrodes. Spectra were recorded with a fiber optic-based CCD spectrophotometer (Ocean Optics, Inc.) in 0.7 second intervals. For determination of the heterogeneous rate constant, $k_{het}$, for Pdx reduction on the electrodes, a potential pulse was applied starting from open circuit to a final voltage in the range from –0.45 to –0.9 V. The decay in absorbance at 458 nm was used to obtain $k_{het}$ according to the correlations developed in Albertson et al., *Anal. Chem.*, 51, 556–560, 1979, the disclosure of which is incorporated herein by reference. The homogeneous (observed) second-order rate constant, $k_{obs}$, for reduced putidaredoxin ($Pdx^1$) and oxidized, camphor-bound CYP101 ($CYP^{os}$) conversion to $Pdx^o$+$CYP^{rs}$ was determined in an anaerobic solution consisting of a Tris-KCl buffer (50 mM Tris-HCl, 0.18 M KCl, 16 mM $MgCl_2$, pH ≈7.4) and an initial protein concentration ratio of [$CYP^{os}$]/[$Pdx^1$]=0.1. A potential pulse was applied starting from open circuit to a final voltage of –0.9 V, and absorbance at 455 nm was used to calculate $k_{obs}$. Comparable results were obtained from the exponential decay of the 392 nm absorbance (after subtracting the Pdx contribution at 392 nm), giving a pseudo-first order rate constant of 0.017 $s^{-1}$ for the conversion of $CYP^{os}$ to $CYP^{rs}$.

Product Analysis

The product, 5-exo-hydroxy-camphor, was identified by GC-MS (gas chromatography and mass spectrophotometry) and quantified by GC-FID (gas chromatography and flame ionization detection). GC injection samples of 1–2 μL were prepared from approximately equal volumes of reaction mixture and an extraction cocktail comprising 0.3 g methylene chloride and 0.02 g KCl with 300 μM n-decane as an internal standard. The GC was operated with a DB-5 column (J&W Scientific, Folsom, Calif.) (30 m) with temperature programing (2 minutes at 60° C., ramp at 10° C./min to 120° C., 2 min at 120° C., ramp up at 15° C./min 160° C.). Retention times (He carrier gas at 2.8 bar pressure) were: n-decane 4.7 minutes, camphor 7.0 minutes, 5-exo-hydroxy-camphor 10.9 minutes. Chromatograms showed peaks for only the internal standard, substrate (camphor) and product (5-exo-hydroxy-camphor, 1 μM minimum detectability). Identification of 5-exo-hydroxy-camphor as the product was done by comparing the m/e (mass/charge ratio) pattern (VG analytical Mass Spectrometer, 70 eV electron impact energy) with published spectra; see White et al., *Arch. Biochem. Biophys*.228, 493–502, 1984, the disclosure of which is incorporated herein by reference.

Example 1

In a 1 cm path-length spectrophotometer cell, with 30 μM Pdx in the above-specified buffer, a potential of –0.7 V (vs. Ag/AgCl) was applied using a potentiostat, and an absorption spectrum was recorded through the transparent $SnO_2$ electrode and 1 cm of reactor solution. The electrode surface area to solution volume ratio was about 5/m. A characteristic absorption spectrum of the oxidized Pdx was recorded initially. After 30 minutes of electrolytic reduction at –0.7 V, a characteristic spectrum of reduced Pdx was recorded. After an additional 30 minutes of electrolysis, the potential was switched to 0 V and a characteristic spectrum of oxidized Pdx was obtained. After electrolysis was complete, 50% of the initial activity of Pdx was recovered, as determined by the method described in Phillips and Langdon, *J. Biol. Chem.*, 237, 2652 (1962), the disclosure of which is incorporated herein by reference. Also, AC and DC voltammetric sweeps across the formal potential of Pdx (E=−0.42 V vs Ag/AgCl) were used to demonstrate the quasi-reversible redox behavior of the process. The recorded current-potential dependencies were stable and reproducible throughout the 6 hour period. This experiment demonstrated the successful utilization of the metal oxide working electrode for continuous electrochemical reduction/oxidation of Pdx. The method described in this Example can be used to determine whether the working electrode has redox activity toward the redox carrier.

Example 2

The same cell as described in Example 1 was equipped with two antimony-doped, tin-oxide electrodes and one platinum wire counter electrode. The reactor solution contained 10 μM CYP101, 118 μM Pdx, 600 μM camphor and 0.2 M KCl, pH 7.4. GC analysis showed the presence of only camphor in the initial solution. Electrolysis was started by applying a potential equal to −0.7 V (vs Ag/AgCl) to the tin oxide electrodes. After 240 minutes of electrolysis, during which the solution was slowly purged with argon gas, GC-MS confirmed the presence of 190 μmoles of the stereospecific product, 5-exo-hydroxy-camphor, the natural product of the CYP101 enzymatic cycle. Therefore, the enzyme underwent about 20 turnovers during the four hour period.

Example 3

The same cell as described in Example 1 was equipped with-one antimony-doped, tin-oxide electrode and a Pt wire counter electrode isolated by a glass frit. A Pt sheet (0.5× 10×30 mm) was positioned close to the surface of the working electrode. The reactor solution contained 0.23 μM CYP101, 108 μM Pdx, 626 μM camphor and 0.16 M KCl+0.01 M MgCl$_2$, pH 7.4. Initial GC analysis indicated no trace of the product. A potential equal to −0.7 V (vs Ag/AgCl) was applied to the tin oxide electrode. The Pt sheet was left at open circuit potential. After 5 hours of electrolysis, during which the solution was stirred by a magnetic stirrer, 442 μM product (5-exo-hydroxy-camphor) was detected by GC analysis. This corresponds to 1922 turnovers of the enzyme at an average rate of 384 turnovers/hour.

Example 4

An antimony-doped, tin-oxide working electrode was wrapped in a Pt grid, which was electrically isolated from the conductive side of the electrode. A Pt wire, isolated from the working electrode and Pt grid by a glass frit, was utilized as a counter electrode. The reactor solution contained 0.2 μM CYP101, 101 μM Pdx, 650 μM camphor and 0.16 M KCl+0.01 M MgCl$_2$, pH 7.4. After 15.5 hours or electrolysis at −0.65 V (vs Ag/AgCl) and room temperature with continuous stirring, the solution contained 222 μM of product (5-exo-hydroxy-camphor), which corresponds to 1127 turnovers of the enzyme. Spectrophotometric analysis taken after electrolysis indicated that about 85 μM of Pdx remained in tact, which corresponds to about 85% of the initial concentration.

Example 5

The reactor solution volume in this experiment was about 20 ml, and two antimony-doped, tin-oxide working electrodes (16 cm$^2$ total reaction surface) were employed. The large solution volume was needed in order to accommodate the combination oxygen/temperature electrode (Orion # 084010) used in some experiments for monitoring the concentration of dissolved oxygen. Two 2 mm diameter Teflon® tubes were inserted through holes in the cover of the cells and served as purging ports. Other experiments were performed in a smaller reactor (1 ml solution volume), which retained the above-described electrode surface area/solution volume ratio, the Pt counter electrode, the Pt grid shielding of the working electrode, stir-bar mixing, solution purging, and head space gas handling. During electrolysis, the potential at the working electrode was maintained at −0.7 V versus the Ag/AgCl reference electrode, while the potential on the counter electrode was adjusted to +1.0 V by controlling the extent of submergence (which directly affected the counter electrode current density) at the fixed working electrode potential. An additional reference electrode was inserted during the adjustment. Although the buffer solution contained a relatively high chloride concentration, chlorine evolution was minimized by holding the counter electrode potential less noble (less positive) than the reversible Cl$^-$/Cl$_2$potential (E$_0$=+1.17 V). In some experiments, the temperature was maintained at 21° C. by air cooling, while in other experiments a water bath was used to control the temperature at 37° C.

Electrolysis experiments were initiated by combining the enzyme components in the Tris/KCl buffer and purging the stirred solution with argon for about 30 minutes at open circuit potential. After extraction of an initial sample (100 μL), the potential of −0.7 V (vs Ag/AgCl) was applied and the argon purge was re-directed to reactor headspace. Solution samples for product analysis were extracted through one of the 2 mm diameter Teflon® tubes.

Table 1 shows data obtained under standard experimental electrolysis reaction conditions, where the buffer comprised 50 mM Tris-HCl, 0.18 KCl, and 16 mM MgCl$_2$. The initial camphor concentration was 800 μM, unless otherwise indicated. The potential was −0.7 V at the tin-oxide working electrode. The temperature was 21–22° C., unless otherwise indicated.

TABLE 1

Camphor Hydroxylation for Several Electroenzymatic Reactor Conditions

| Reactor Solution Composition | Oxygen Conditon | Product Turnover Rate* |
|---|---|---|
| 41 μM Pdx | Argon Purge | 0 |
| 12.8 μM CYP101 | Argon Purge | 0 |
| 41 μM Pdx + 0.41 μM CYP101 | Air Saturated | 0.9 |
| 55 μM Pdx + 0.18 μM CYP101 | Argon Purge | 4.2 |
| 108 μM Pdx + 0.23 μM CYP101 | Argon Purge | 6.4 |
| 1030 μM Pdx + 0.13 μM CYP101† | Argon Purge | 34 |
| 1030 μM Pdx + 0.13 μM CYP101‡ | Argon Purge | 36 |

*nmol 5-exo-hydroxy-camphor/min/nmol CYP101
†standard conditions except initial camphor concentration was 2 mM
‡standard conditions except initial camphor concentration was 2 mM and temperature was 37° C.

The invention has been described in preferred and exemplary embodiments and aspects, but is not limited thereto. Persons skilled in the art will appreciate that other modifications and applications fall within the scope of the invention. When the term "about" is used in the specification and claims in connection with a range of numbers, it is intended to modify both the low value and the high value of the range.

We claim:
1. An electroenzymatic reactor, comprising:
a reaction vessel;
a working electrode compartment, within the vessel;

a reactor solution comprising a redox enzyme, a redox carrier, and an oxidizable or reducible compound, within the working electrode compartment;

a metal oxide working electrode within the working electrode compartment, having a redox potential close to that of the redox carrier, and a counter electrode, outside the working electrode compartment.

2. An electroenzymatic reactor according to claim 1, wherein the compound is an oxidizable compound.

3. An electroenzymatic reactor according to claim 1, wherein the redox enzyme and redox carrier are each at least about 95% pure.

4. An electroenzymatic reactor according to claim 1, wherein the redox enzyme and redox carrier are each at least about 97% pure.

5. An electroenzymatic reactor according to claim 1, wherein the working electrode is made of at least one material selected from the group consisting of antimony-doped tin oxide, fluorine-doped tin oxide, indium-tin oxide, titanium oxide, zinc oxide, iridium oxide, and ruthenium oxide.

6. An electroenzymatic reactor according to claim 1, wherein the working electrode is made of antimony-doped tin oxide.

7. An electroenzymatic reactor according to claim 1, wherein the counter electrode is made of at least one material selected from the group consisting of platinum-group metals, metal oxides, and carbon-based materials.

8. An electroenzymatic reactor according to claim 1, wherein the counter electrode is made of at least one material selected from the group consisting of platinum, palladium, ruthenium, ruthenium oxide, glass carbon, reticulated carbon, and titanium dioxide.

9. An electroenzymatic reactor according to claim 1, wherein the counter electrode is made of platinum.

10. An electroenzymatic reactor according to claim 1, wherein the working electrode is made from antimony-doped tin oxide and the counter electrode is made from platinum.

11. An electroenzymatic reactor according to claim 10, wherein the ratio of the surface area of the working electrode to the surface area of the counter electrode is within the range of about 8:1 to 10:1.

12. An electroenzymatic reactor according to claim 1, wherein the counter electrode is separated from the working electrode compartment by a gas permeable separator.

13. An electroenzymatic reactor according to claim 1, wherein molecular oxygen is supplied to the working electrode compartment by water electrolysis on the counter electrode.

14. An electroenzymatic reactor according to claim 13, further comprising a cover that prevents the flow of atmospheric oxygen into the working electrode compartment and permits escape of purging gas.

15. An electroenzymatic reactor according to claim 13, further comprising at least one inert gas inlet.

16. An electroenzymatic reactor according to claim 1, wherein the redox enzyme is cytochrome or a mutant thereof and the redox carrier is putidaredoxin or a mutant thereof.

17. An electroenzymatic reactor according to claim 16, wherein the working electrode is set at a potential ranging from about −0.5 V to −0.9 V versus a Ag/AgCl reference electrode.

18. An electroenzymatic reactor according to claim 1, wherein the working electrode is set at a potential of about −0.7 V versus a Ag/AgCl reference electrode.

19. An electroenzymatic reactor according to claim 1, further comprising a buffer solution containing chloride ions within the vessel.

20. An electroenzymatic reactor according to claim 19, wherein the buffer solution comprises a solution of KCl and $MgCl_2$.

21. An electroenzymatic reactor according to claim 19, wherein the buffer solution comprises a frozen aqueous phase in equilibrium with a liquid organic phase.

22. An electroenzymatic reactor according to claim 1, wherein the working electrode compartment further comprises a screen near, but not contacting, the working electrode, wherein the screen catalyzes the decomposition of hydrogen peroxide that originates during oxygen reduction at the working electrode.

23. An electroenzymatic reactor according to claim 22, wherein the screen is made of a non-corrosive metal selected from the group consisting of platinum, iridium, nickel, rhodium and cobalt.

24. An electroenzymatic reactor according to claim 22, wherein the screen is made of platinum.

25. An electroenzymatic reactor according to claim 1, wherein the reactor further comprises a screen near, but not contacting, the counter electrode, wherein the screen catalyzes the decomposition of hydrogen peroxide that originates during oxygen reduction at the counter electrode.

26. An electroenzymatic reactor according to claim 25, wherein the screen is made of a non-corrosive metal selected from the group consisting of platinum, iridium, nickel, rhodium and cobalt.

27. An electroenzymatic reactor according to claim 25, wherein the screen is made of platinum.

28. An electroenzymatic reactor for oxidizing or reducing a substrate, comprising:

a reaction vessel;

a working electrode compartment, within the vessel;

a reactor solution comprising a redox enzyme, a redox carrier, and an oxidizable or reducible substrate, within the working electrode compartment;

a working electrode within the working electrode compartment, that directly transfers electrons to or directly removes electrons from the redox carrier;

a counter electrode within the vessel that supplies molecular oxygen or hydrogen to the working electrode compartment by water electrolysis reaction; and a cover that prevents the flow of atmospheric oxygen into the working electrode compartment and permits escape of purging gas.

29. An electroenzymatic reactor according to claim 28, wherein the substrate is an oxidizable substrate and all molecular oxygen necessary for oxidizing the substrate is supplied by the counter electrode.

30. An electroenzymatic reactor according to claim 28, wherein the substrate is a reducible substrate and all molecular hydrogen necessary for reducing the substrate is supplied by the counter electrode.

31. An electroenzymatic reactor according to claim 28, wherein the counter electrode is separated from the working electrode compartment by a gas permeable separator.

32. An electroenzymatic reactor according to claim 28, further comprising at least one inert gas inlet.

33. An electroenzymatic reactor according to claim 28, wherein the counter electrode is made of at least one material selected from the group consisting of platinum-group metals, metal oxides, and carbon-based materials.

34. An electroenzymatic reactor according to claim 28, wherein the counter electrode is made of at least one material selected from the group consisting of platinum and ruthenium.

35. An electroenzymatic reactor, comprising:

a working electrode compartment;

a reactor solution comprising a redox enzyme, a redox carrier, and an oxidizable or reducible substrate, within the working electrode compartment;

a working electrode made of a least one material selected from the group consisting of antimony-doped tin oxide, fluorine-doped tin oxide, indium-tin oxide, titanium oxide, zinc oxide, iridium oxide, and ruthenium oxide, within the working electrode compartment; and a counter electrode made of at least one material selected from the group consisting of platinum group metals, metal oxides, and carbon-based materials.

36. An electroenzymatic reactor, comprising:

a reaction vessel;

a working electrode compartment within the vessel;

a reactor solution comprising a redox enzyme, a redox carrier, and an oxidizable or reducible substrate, within the working electrode compartment;

a working electrode that directly transfers electrons to or directly removes electrons from the redox carrier, within the working electrode compartment;

a counter electrode within the reaction vessel, one of said working electrode and counter electrode having a more negative potential; and a screen near, but not contacting, the electrode having a more negative potential, wherein the screen catalyzes the decomposition of hydrogen peroxide that originates during oxygen reduction at the electrode having a more negative potential.

37. An electroenzymatic reactor according to claim 36, wherein the screen is made of a non-corrosive metal selected from the group consisting of platinum, iridium, nickel, rhodium and cobalt.

38. An electroenzymatic reactor according to claim 36, wherein the screen is made of platinum.

39. An electroenzymatic reactor according to claim 36, wherein the screen has a surface area greater than or equal to the surface area of the working electrode.

* * * * *

UNITED STATES PATENT AND TRADEMARK OFFICE
CERTIFICATE OF CORRECTION

PATENT NO. : 6,126,795
DATED : October 3, 2000
INVENTOR(S) : Vytautas P. Reipa and Vincent L. Vilker It is certified that error appears in the above-identified patent and that said Letters Patent is hereby corrected as shown below:

Column 13,
Line 65, replace "according to claim 1" with -- according to claim 16 --.

Signed and Sealed this

Eleventh Day of February, 2003

JAMES E. ROGAN
*Director of the United States Patent and Trademark Office*